Figure 1:
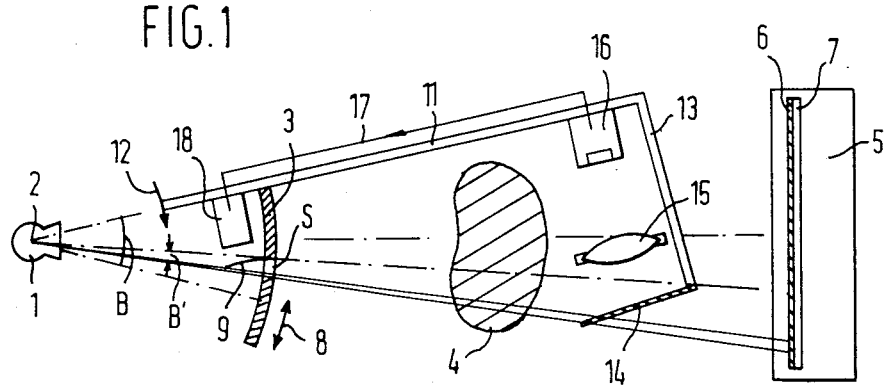

United States Patent [19]

Duinker et al.

[11] Patent Number: 4,675,893
[45] Date of Patent: Jun. 23, 1987

[54] APPARATUS FOR SLIT RADIOGRAPHY

[75] Inventors: Simon Duinker, Bloemendaal; Hugo Vlasbloem, Maasland, both of Netherlands

[73] Assignee: N.V. Optische Industrie "De Oude Delft", Netherlands

[21] Appl. No.: 713,199

[22] Filed: Mar. 18, 1985

[30] Foreign Application Priority Data

Mar. 16, 1984 [NL] Netherlands ......................... 8400845

[51] Int. Cl.⁴ ............................................. G21K 1/04
[52] U.S. Cl. .................................... 378/151; 378/145; 378/147; 378/150; 378/153; 378/146
[58] Field of Search ................................ 378/145–148, 378/150–153, 156–158

[56] References Cited

U.S. PATENT DOCUMENTS

| 1,164,987 | 12/1915 | Bucky | 378/145 |
| 3,101,407 | 8/1963 | Shipman, Jr. | 378/146 |
| 3,755,672 | 8/1973 | Edholm et al. | 378/151 |
| 4,132,895 | 1/1979 | Froggatt | 378/146 |
| 4,442,538 | 4/1984 | Haendle | 378/146 |
| 4,547,893 | 10/1985 | Gordon | 378/4 |

FOREIGN PATENT DOCUMENTS 2345406 7/1975 Fed. Rep. of Germany ...... 378/150

Primary Examiner—Craig E. Church
Assistant Examiner—John C. Freeman
Attorney, Agent, or Firm—Louis E. Marn

[57] ABSTRACT

An apparatus for slit radiography comprising an X-ray source by means of which a body being irradiated can be scanned through a slit diaphragm by a substantially planar, fan-shaped X-ray beam, the scanning X-ray beam passed through the body impinging upon an X-ray detector. The apparatus comprises controllable attenuation elements coacting with the slit diaphragm, each element being adapted to influence a sector of the scanning X-ray beam under the control of signals generated by a radiation detector device. The radiation detector device is disposed between the body being irradiated and the X-ray detector. The radiation detector device comprises at least one radiation detector extending at any moment into the scanning X-ray beam passed through the body and moving in synchronism with the scanning movement of the X-ray beam. The radiation detector device is divided into sections corresponding with the sectors of the scanning X-ray beam influenceable by the attenuation elements, while, in operation, each section of the radiation detector device generates a signal usable for controlling the attenuation elements.

13 Claims, 5 Drawing Figures

APPARATUS FOR SLIT RADIOGRAPHY

The present invention relates to an apparatus for slit radiography comprising an X-ray source by means of which a body being irradiated can be scanned through a slit diaphragm by a substantially planar, fan-shaped X-ray beam, while the scanning X-ray beam passed through the body impinges upon an X-ray detector.

Such an apparatus, comprising controllable attenuation elements coacting with a slit diaphragm, is described in copending Dutch patent application No. 8400845, which is incorporated herein by reference. Dutch patent application No. 8400845 describes several methods of generating control signals required for the attenuation elements. In most cases described in Dutch patent application No. 8400845, use is made for that purpose of a series of light detectors placed at the exit side of the X-ray detector device employed; each light detector corresponds with a section of the slit diaphragm and controls, through control means, the attenuation element coacting with said section, or a group of attenuation elements coacting with said section.

However, this technique cannot be applied in a simple manner when a lighttight X-ray film cassette is employed as X-ray detector.

Consequently, it is an object of the present invention to design an apparatus for slit radiography comprising controllable attenuation elements coacting with a slit diaphragm in such a manner that, even when a lighttight X-ray film cassette is employed, the control signals required for the attenuation elements are obtained in a relatively simple and reliable manner.

To this effect according to the present invention, an apparatus of the above described type is characterized in that it comprises controllable attenuation elements coacting with the slit diaphragm, each element being adapted to influence a sector of the scanning X-ray beam under the control of signals generated by a radiation detector device; that the radiation detector device is disposed between the body being irradiated and the X-ray detector; that the radiation detector device comprises at least one radiation detector extending at any moment into the scanning X-ray beam passed through the body and moving in synchronism with the scanning movement of the X-ray beam. The radiation detector device is divided into sections corresponding with the sectors of the scanning X-ray beam influenceable by the attenuation elements, while in operation, each section of the radiation detector device generates a signal usable for controlling the attenuation elements.

It is observed that the present invention can be used both in case a lighttight X-ray film cassette and in case any other type of X-ray detector is employed.

Figure 2:
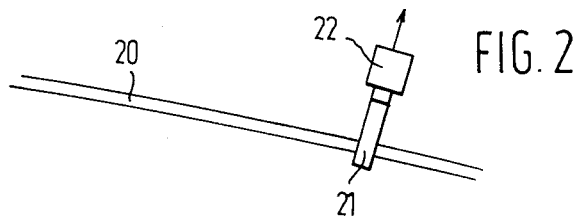
Figure 3:
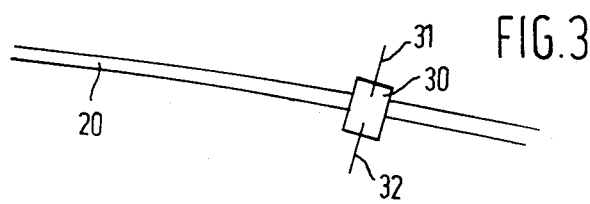
Figure 4:
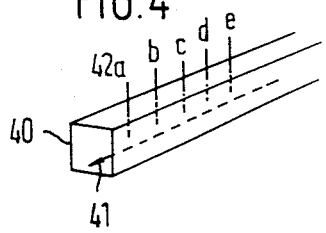
Figure 5:
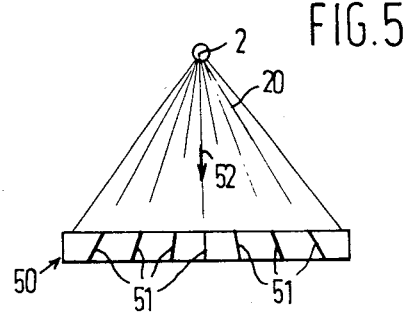

Some embodiments of the apparatus according to the present invention will now be described, by way of example, with reference to the accompanying drawing, in which:

FIG. 1 diagrammatically shows a first embodiment of an apparatus according to the present invention;
FIG. 2 diagrammatically shows a variant of FIG. 1;
FIG. 3 shows another variant of FIG. 2;
FIG. 4 shows a modification of FIG. 3; and
FIG. 5 shows a modification of FIG. 4.

FIG. 1 diagrammatically shows a first embodiment of the present invention, showing an X-ray source 1 having an X-ray focal point 2. The X-ray source, in operation, generates an X-ray beam B, a substantially planar fan-shaped portion B' of which in principle can pass through the slit S of a slit diaphragm 3. Furthermore, the figure shows a body being irradiated 4 and an X-ray detector 5 placed behind said body, said detector 5 being positioned in a casing, not shown. The X-ray detector may be of any conventional type, but is formed in the present embodiment by a lighttight X-ray film cassette containing an X-ray fluorescent screen 6 and an X-ray film 7 placed therebehind. In certain X-ray film cassettes, there is arranged behind the X-ray film a second X-ray fluorescent screen. Instead of such a film cassette, e.g. also a stationary X-ray image intensifier tube with large entrance screen or an X-ray image intensifier tube with a strip-like entrance screen can be employed. In the latter case, the X-ray image intensifier tube, in operation, performs a scanning movement.

In the situation shown, the X-ray beam B' passed through the slit diaphragm only irradiates a strip-like part of the body 4, which is imaged on the entrance screen of the X-ray detector, as shown at 10. In order to obtain an image of a larger part of the body, the X-ray beam is adapted to effect a scanning movement in the plane of drawing. This can be effected in different manners not forming part of the present invention, e.g. by having the slit diaphragm perform a movement indicated by an arrow 8. The slit diaphragm coacts with a plurality of controllable attenuation elements 9. The attenuation elements are juxtaposed and may be disposed e.g. on one of the edges in such a manner that the attenuation elements can extend, under the influence of suitable control signals, to a greater or lesser extent, into the beam B' passed or to be passed through the slit S. Thus, the X-ray beam can be attenuated instantaneously and locally to a greater or lesser extent, as described in Dutch patent application No. 8400845. It is observed that the slit of the slit diaphragm may occupy a horizontal, vertical or intermediate position, while the scanning is effected in vertical, horizontal or intermediate direction.

The attenuation elements should be controlled in dependence on the intensity of the X-rays passed through the body. According to the present invention, use is made therefore of a radiation detector device provided between the body 4 being irradiated and the X-ray detector, said radiation detector device being arranged in such a manner that the radiation passed through the body at any moment can be detected, i.e. for each sector of the X-ray beam passed through the body separately, corresponding with an attenuation element 9 or with a group of such attenuation elements.

According to the present invention, use is made therefore of a radiation detector device performing between the body and the X-ray detector a scanning movement in synchronism with the scanning movement effected, in operation, by the X-ray beam B'.

To this effect, the radiation detector device is coupled mechanically or electromechanically to the means effecting that the X-ray beam performs a scanning movement. The radiation detector device may e.g. be placed before the X-ray detector 5 and, in operation, perform a vertical scanning movement.

In the embodiment shown in FIG. 1, the radiation detector device is attached to an arm 11 extending from the slit diaphragm in the direction of the X-ray detector. The arm, as indicated by an arrow 12, is adapted to swivel relatively to a real or a virtual swivelling axis extending perpendicular to the plane of drawing through the X-ray focal point 2. The arm is at any moment beyond the X-ray beam passed through the slit diaphragm. The arm 11 may be suitably affixed to the slit diaphragm, as shown in FIG. 1, so that synchronism of the arm movement with the movement of the slit diaphragm (and hence also the scanning movement of the X-ray beam) is ensured. Such a fixed connection of the arm to the slit diaphragm, however, is not essential. Of importance is only that the arm moves in synchronism with the X-ray beam B'.

The arm extends beyond the body being irradiated and is provided at the end extending beyond the body with a depending arm 13, which carries an X-ray fluorescent screen 14 at the end distal from the arm 11.

The X-ray fluorescent screen 14 extends at least partly at any moment into the X-ray beam passed through the body and forms the radiation detector proper. The depending arm 13 also carries a series of juxtaposed lenses 15. The number of lenses 15 corresponds with the number (groups of) attenuation elements. The lenses are mounted on the depending arm 13 in such a manner that the lenses are present at any moment beyond the X-ray beam passed through the body. Each lens is adapted to collect the light generated in a given sector of the X-ray fluorescent screen under the influence of X-radiation impinging upon the X-ray fluorescent screen.

Said sectors correspond again with the sectors of the X-ray beam B' passed or to be passed through the slit diaphragm and influenceable by an attenuation element 9 or a group of attenuation elements.

Each lens is adapted to bundle the light collected on a corresponding signal transmitter 16 likewise attached to the assembly of arms 11, 13, e.g. a photodetector transmitting an electric signal corresponding with the luminance of the light. Said electric signal is applied via a line 17 to a control device 18 shown diagrammatically. Control device 18 forms from the signals received control signals for the attenuation element corresponding with the light detector concerned.

The fluorescent screen 14, in the embodiment shown, is mounted at an angle to the scanning X-ray beam, so that a relatively high light output is obtained with a relatively thin screen. However, this is not essential. Naturally, the fluorescent screen should be designed so as to minimally attenuate the scanning X-ray beam.

The X-ray fluorescent screen 14 may be a screen extending in a direction transverse to the plane of drawing, but if a better separation between the various sectors of the X-ray beam is desired, the screen may also consist of a plurality of juxtaposed but mutually separated screen portions.

FIG. 2 diagrammatically shows a variant of the radiation detector device shown in FIG. 1, wherein the arms 11, 13 or similar, corresponding members have been omitted. The scanning X-ray beam passed through the slit diaphragm is indicated in FIG. 2 at 20. Before impinging upon the X-ray film cassette 7 or another imaging X-ray detector, the X-ray beam 20 passes a series of juxtaposed scintillation crystal elements 21, one being shown in FIG. 2, for which may be used e.g. germanium iodide crystals, which produce light under the influence of X-radiation. Each scintillation crystal element is coupled optically to a photodetector 22 producing, in response to the associated scintillation crystal element, an electric signal which can be used again for forming a control signal for a corresponding attenuation element or a corresponding group of attenuation elements.

To increase the effective light output of the scintillation crystal elements, each scintillation crystal element, preferably on all sides, except the photodetector-coupled side, is provided with a layer reflecting on the inside. Such a layer at the same time protects the scintillation crystal element against external influences, such as the action of moisture, which is of relevance, since scintillation crystals mostly have hygroscopic properties.

FIG. 3 shows a second variant of the radiation detector device according to the present invention. The scanning X-ray beam is again indicated at 20. Instead of a series of scintillation crystal elements, there is now employed a series of juxtaposed ionization chambers 30, one being shown diagrammatically. Each ionization chamber comprises two electrodes 31, 32. There prevails a voltage differential between the electrodes. When the ionization chamber is irradiated by energy-rich radiation, such as X-radiation, this will result in a current flowing in the electric circuit connected to the electrodes 31, 32, from which, again, control signals for one or more corresponding attenuation elements can be derived.

Naturally, at least the front and rear wall, as viewed in the direction of the scanning beam 20, should be made of material not or hardly attenuating X-radiation.

Instead of a plurality of separate ionization chambers, also a single elongate ionization chamber can be used which is provided with one common electrode extending along the entire length of the ionization chamber, i.e. transversely to the plane of drawing, and a plurality of separate electrodes from which electrodes control signals for the corresponding attenuation elements are derived.

Such an elongate ionization chamber is shown in FIG. 4 and indicated at 40. The common electrode is indicated at 41 and the electrodes opposite the common electrode are indicated at 42a . . . e. The common electrode can be considered to be an interconnection of a plurality of separate electrodes. Such an interconnection can be positioned both in the elongate ionization chamber and outside said chamber.

A mixed form between the embodiments of a radiation detector shown in FIGS. 3 and 4 is shown in top view in FIG. 5. An elongate ionization chamber 50 contains a plurality of partitions 51 of synthetic plastics material, e.g. Mylar. The compartments between the partitions again form the ionization chamber. The scanning X-ray beam 20 is shown in top view and has the direction indicated by an arrow 52. The partitions are directed preferably at the X-ray focal point 2.

It is observed that, after the foregoing, various modifications will readily occur to one skilled in the art. Such modifications are deemed not to depart from the scope of the present invention.

What we claim:

1. An apparatus for slit radiography, which comprises:
   an X-ray source;
   an X-ray detector collecting radiation passing through a body to be radiographed;
   a slit diaphragm positioned between said X-ray source and said body for forming a planar X-ray beam;
   a plurality of attenuating elements positioned along said slit diaphragm forming a plurality of attenuating sections;

means for scanning said body with said planar X-ray beam;

detection member comprising a plurality of response sections juxtaposed along a direction of said slit diaphragm, each of said response sections being responsive to radiation from said X-ray source to produce an electric signal representative of intensity, each of said response sections of said detection member corresponding to a respective attenuating section of said plurality of attenuating sections;

means for moving said detection member in synchronization with said means for scanning said body with said planar X-ray beam; and means for simultaneously controlling each of said attenuating elements during scanning of said body in response to said electric signal produced at a respective response section.

2. The apparatus as defined in claim 1 wherein said detection member is comprised of an X-ray fluorescent screen and a plurality of juxtaposed lenses disposed beyond said scanning planar X-ray beam, each of said plurality of lenses being able to collect the light generated in a given sector of said X-ray fluorescent screen in response to said scanning planar X-ray beam and to direct said generated light to an associated photodetector to convert said generated light into an electric signal.

3. The apparatus as defined in claim 2 wherein said X-ray fluorescent screen is divided into a plurality of juxtaposed, mutually separated sectors.

4. The apparatus as defined in claim 2 wherein said X-ray fluorescent screen extends at an acute angle into said scanning planar X-ray beam.

5. The apparatus as defined in claim 1 wherein said detection member comprises a plurality of juxtaposed scintillation crystal elements, each of said plurality of juxtaposed scintillation crystal elements being coupled optically to a photodetector to produce an electric signal.

6. The apparatus as defined in claim 5 wherein each of said plurality of juxtaposed scintillation crystal elements is provided with an internally reflecting layer on an entire outer surface thereof except for a portion optically coupled to said photodetector.

7. The apparatus as defined in claim 1 wherein said detection member is comprised of a plurality of juxtaposed ionization chambers, each of said plurality of juxtaposed ionization chambers having opposed electrodes to develop a current from which is derived said electric signal.

8. The apparatus as defined in claim 7 wherein said plurality of juxtaposed ionization chambers are combined into a single elongate ionization chamber having a plurality of spaced apart electrodes and a common second electrode.

9. The apparatus as defined in claim 8 wherein a partition is placed in said elongate ionization chamber between each pair of adjoining first electrodes.

10. The apparatus as defined in claim 9 wherein said partition is directed towards a focal point of said X-ray source.

11. The apparatus as defined in claim 1 wherein said detection member is attached to an arm member extending from said slit diaphragm to beyond said body being radiographed, said arm being swivellable in a vertical and horizontal plane relatively to a line extending horizontally and vertically, respectively, through a focal point of said X-ray source.

12. The apparatus as defined in claim 11 wherein said arm member includes a depending arm portion for said detection member.

13. The apparatus as defined in claim 12 wherein said detection member is positioned on an end of said depending arm portion proximal to said X-ray detector.

* * * * *